(12) United States Patent
Steszyn et al.

(10) Patent No.: US 8,453,346 B2
(45) Date of Patent: *Jun. 4, 2013

(54) ORTHOTIC FOOT DEVICE WITH REMOVABLE SUPPORT COMPONENTS AND METHOD OF MAKING SAME

(75) Inventors: Michael Steszyn, Portland, OR (US); Simon Luthi, Lake Oswego, OR (US); Joseph F. McMillan, Portland, OR (US); Peter Valois, Portland, OR (US); Martin Trautmann, Munich (DE); Damian Donzis, San Diego, CA (US); Aimee Donzis, San Diego, CA (US); Ronald Charles Irani, Felsted (GB)

(73) Assignee: Orthosole Limited, A Guernsey Limited Company, Saint Peter Port, Guernsey (GB)

( * ) Notice: Subject to any disclaimer, the term of this patent is extended or adjusted under 35 U.S.C. 154(b) by 833 days.

This patent is subject to a terminal disclaimer.

(21) Appl. No.: 12/196,113

(22) Filed: Aug. 21, 2008

(65) Prior Publication Data

US 2009/0049712 A1 Feb. 26, 2009

Related U.S. Application Data

(60) Provisional application No. 60/965,994, filed on Aug. 24, 2007.

(51) Int. Cl.
*A43B 7/14* (2006.01)
*A43B 13/38* (2006.01)

(52) U.S. Cl.
USPC ...................... 36/44; 36/91; 36/146

(58) Field of Classification Search
USPC .............. 36/91, 92, 43, 44, 71, 142, 160, 146
See application file for complete search history.

(56) References Cited

U.S. PATENT DOCUMENTS

| 3,084,695 | A | * | 4/1963 | O'Donnell | 36/174 |
|---|---|---|---|---|---|
| 3,992,788 | A | | 11/1976 | Orien et al. | |
| 4,597,196 | A | * | 7/1986 | Brown | 36/44 |
| 4,603,698 | A | | 8/1986 | Cherniak | |
| 4,793,078 | A | | 12/1988 | Andrews | |
| 4,841,648 | A | | 6/1989 | Shaffer et al. | |
| 5,138,774 | A | * | 8/1992 | Sarkozi | 36/164 |
| 5,438,768 | A | * | 8/1995 | Bauerfeind | 36/44 |
| 5,961,477 | A | | 10/1999 | Turtzo | |
| 5,976,100 | A | * | 11/1999 | Greenawalt | 602/66 |
| 6,000,147 | A | | 12/1999 | Kellerman | |
| 6,101,743 | A | | 8/2000 | Brown | |
| 6,105,283 | A | | 8/2000 | Park | |
| 6,176,025 | B1 | * | 1/2001 | Patterson et al. | 36/28 |
| 6,557,273 | B2 | | 5/2003 | Polifroni | |

(Continued)

FOREIGN PATENT DOCUMENTS

| DE | 3131163 A1 | 3/1983 |
|---|---|---|
| WO | WO 93/13685 A1 | 7/1993 |

*Primary Examiner* — Jila M Mohandesi
(74) *Attorney, Agent, or Firm* — Bernard L. Kleinke; Duckor Spradling Metzger & Wynne

(57) ABSTRACT

An orthotic foot device for footwear may include a flexible insole chassis adapted to extend substantially between the heel and the toe of the footwear and at least one support component attached at a lower side of the chassis. The chassis may include a cushioned layer composed of conforming resilient material overlying the upper side of the chassis.

15 Claims, 14 Drawing Sheets

U.S. PATENT DOCUMENTS

| | | |
|---|---|---|
| 6,804,902 B1 | 10/2004 | McCracken et al. |
| 6,854,199 B2 | 2/2005 | Polifroni |
| 7,020,990 B2 * | 4/2006 | Khoury .......................... 36/154 |
| 7,104,704 B2 | 9/2006 | Matsumoto et al. |
| 7,124,520 B2 | 10/2006 | Galbraith et al. |
| 7,210,250 B2 | 5/2007 | Gallegos |
| 7,484,319 B2 * | 2/2009 | Cheskin et al. .................. 36/44 |
| 7,900,380 B2 * | 3/2011 | Rich .............................. 36/154 |
| 8,250,783 B2 * | 8/2012 | Luthi et al. ...................... 36/44 |
| 2004/0194344 A1 | 10/2004 | Tadin |
| 2006/0059726 A1 * | 3/2006 | Song et al. ..................... 36/142 |
| 2007/0043582 A1 | 2/2007 | Peveto et al. |
| 2007/0084084 A1 | 4/2007 | Rich |
| 2007/0180632 A1 | 8/2007 | Gallegos |
| 2007/0204484 A1 * | 9/2007 | Davis ............................... 36/44 |

* cited by examiner

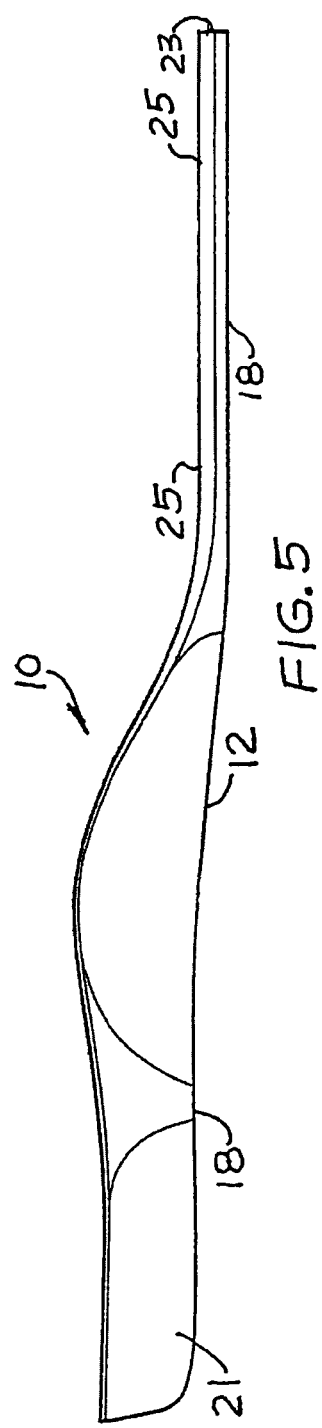
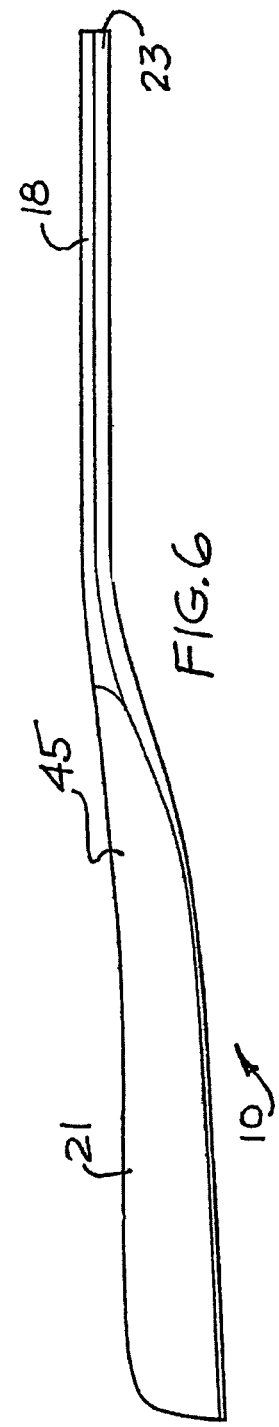

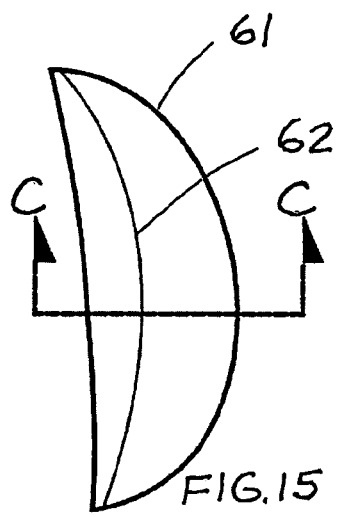
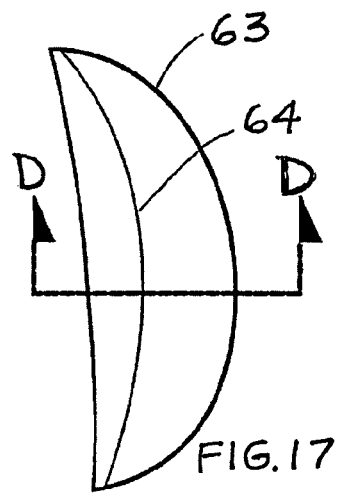
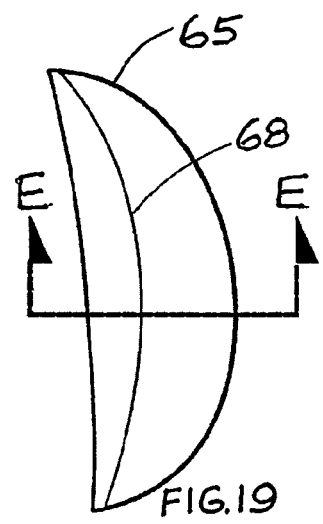
FIG. 15  FIG. 17  FIG. 19
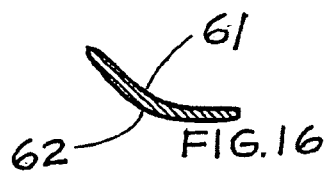
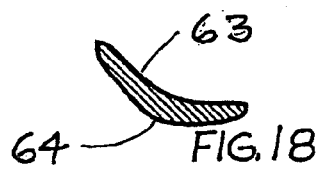
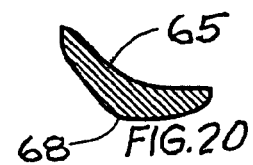
FIG. 16  FIG. 18  FIG. 20

ORTHOTIC FOOT DEVICE WITH REMOVABLE SUPPORT COMPONENTS AND METHOD OF MAKING SAME

RELATED APPLICATION

This application claims priority to U.S. provisional patent application, entitled ORTHOTIC FOOT DEVICE (INSOLE) WITH ADJUSTABLE METATARSAL AND ARCH SUPPORT, Application No. 60/965,994, filed Aug. 24, 2007.

FIELD OF THE INVENTION

The present invention relates in general to an orthotic device. It more particularly relates to an orthotic foot device with removable support components and method of making same.

BACKGROUND ART

There is no admission that the background art disclosed in this section legally constitutes prior art.

There have been many different types and kinds of orthotic devices for foot war. For example, reference may be made to U.S. Pat. Nos. 3,992,788; 4,603,698; 4,793,078; 4,841,648; 5,746,011; 6,105,283; 6,557,273; 6,804,902; 6,854,199; 7,107,704; 7,124,520; and 7,210,250; and U.S. Patent Application Publication Nos. 2004/0194344; 2007/0043582; 2007/0084084; and 2007/0180632.

There have been removable insoles for shoes, where the insoles employ removable support components. The support components are attached to a top or upper portion of the insole such that the support components are directly adjacent the bottom of the wearer's foot for supporting portions of the foot such as the arch. Such an arrangement may adversely affect the comfort and wearability of the insole.

BRIEF DESCRIPTION OF THE DRAWINGS

The features of this invention and the manner of attaining them will become apparent, and the invention itself will be best understood by reference to the following description of certain embodiments of the invention taken in conjunction with the accompanying drawings, wherein:

FIGS. 5 and 6 are enlarged side elevational views of the orthotic foot device of FIG. 1;

FIG. 15 is a top view of the arch support of FIG. 13, which provides light support;

FIG. 16 is a sectional view of the arch support of FIG. 15 taken along lines C-C thereof;

FIG. 17 is a top view of another arch support, which provides medium support for the orthotic foot device of FIG. 1;

FIG. 18 is a sectional view of the arch support of FIG. 17 taken along lines D-D thereof;

FIG. 19 is a top view of a further arch support, which provides firm support for the orthotic foot device of FIG. 1;

FIG. 20 is a sectional view of the arch support of FIG. 19 taken along lines E-E thereof;

DETAILED DESCRIPTION OF CERTAIN EMBODIMENTS OF THE INVENTION

Figure 1:
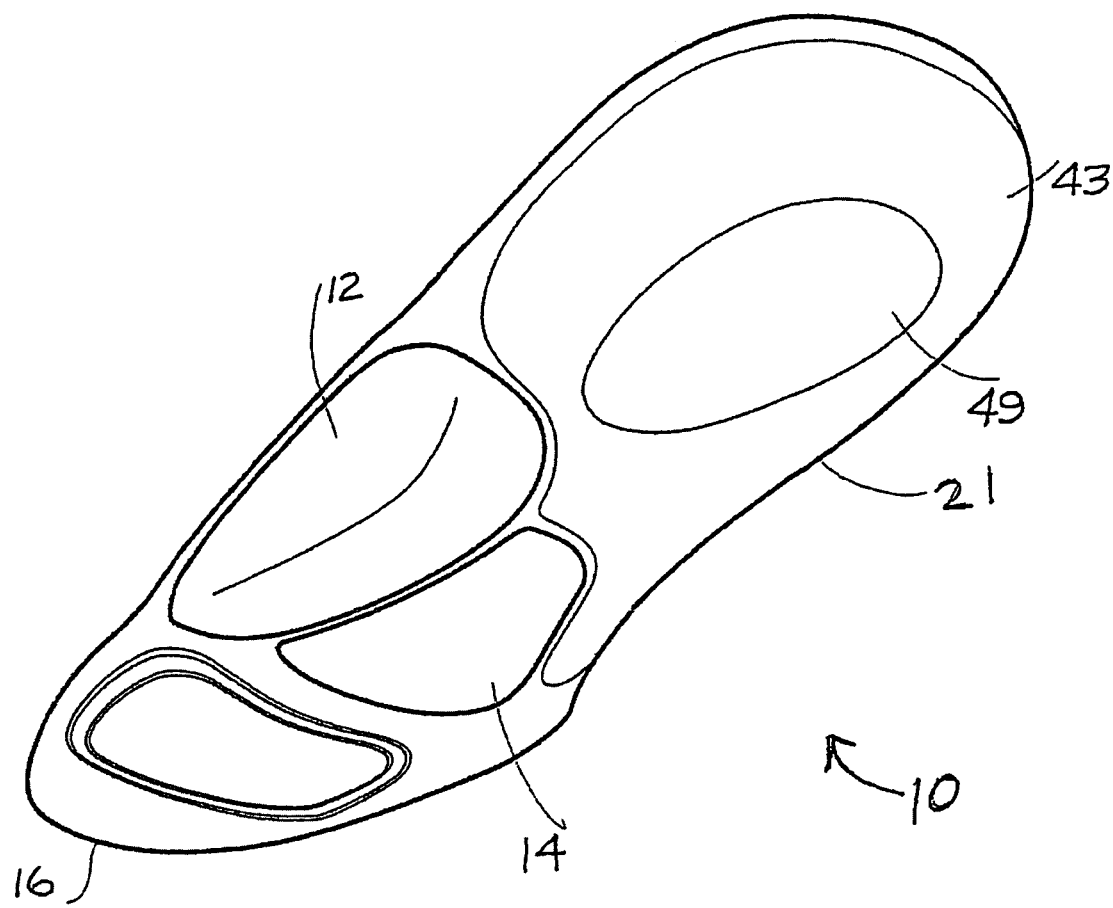
FIG. 1 is a pictorial view of an orthotic foot device with a pair of removable support components according to an embodiment of the present invention.
Figure 2:
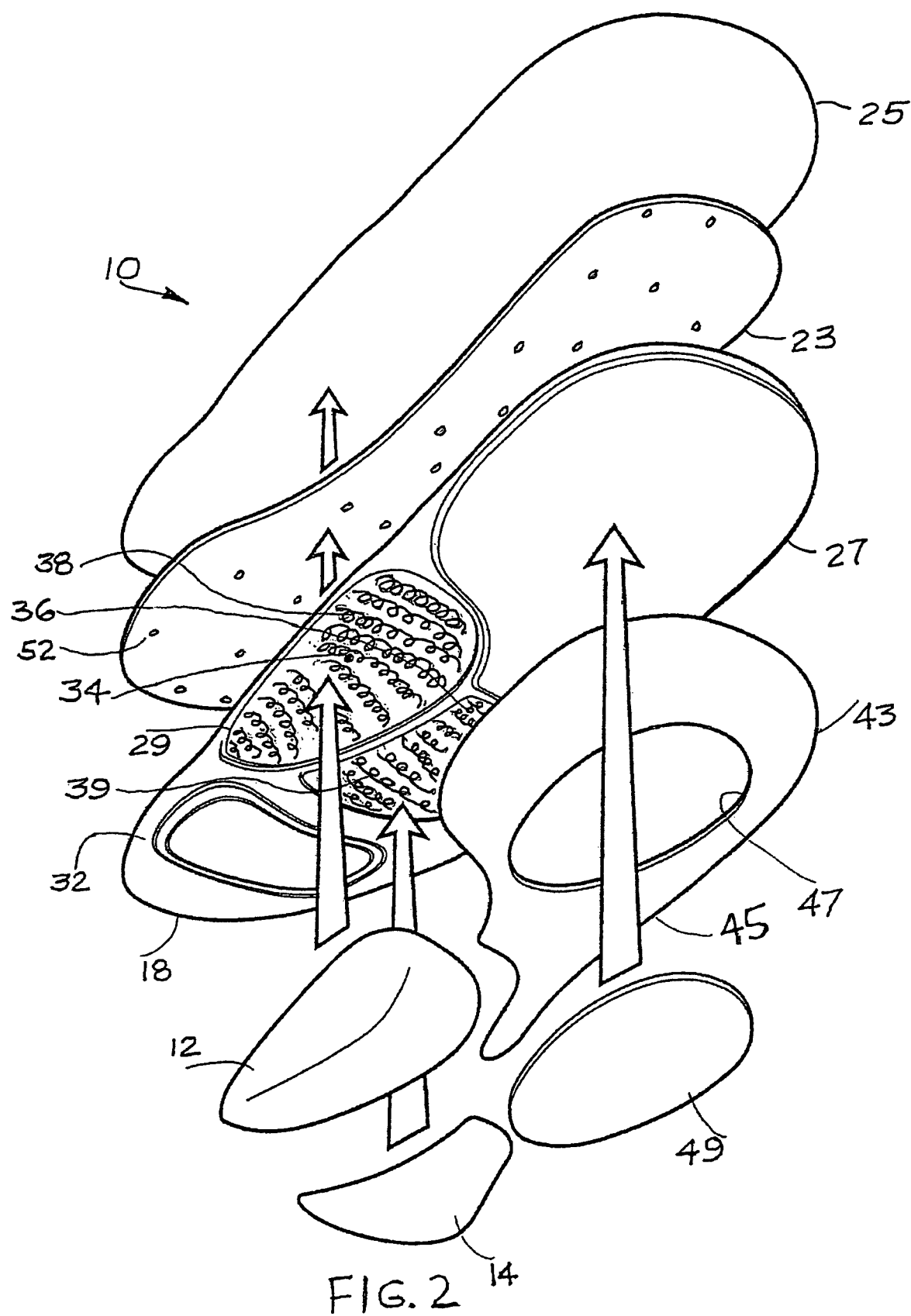
FIG. 2 is an exploded view of the orthotic foot device of FIG. 1.

It will be readily understood that the components of the embodiments as generally described and illustrated in the drawings herein, could be arranged and designed in a wide variety of different configurations. Thus, the following more detailed description of the embodiments of the system, components and method of the present invention, as represented in the drawings, is not intended to limit the scope of the invention, as claimed, but is merely representative of the embodiments of the invention.

An embodiment of the orthotic foot device and method of making it is disclosed herein. The device provides support for the foot when used in footwear, in certain regions of the foot such as in the arch and metatarsal regions, in a manner that is very comfortable and yet supportive to the wearer. The embodiment of the orthotic foot device may provide at least one secure, but easily adjusted support component for a region of the foot such as the arch and metatarsal regions. The support component may be removably attached to a cushioned supportive footbed or chassis to provide an increased walking/running comfort and performance. It will become apparent to those skilled in the art that at least one of the support components may be fixedly or integrally attached to the footbed or chassis.

In accordance with certain embodiments of the present invention, there is provided an orthotic foot device for footwear such as a shoe having a heel and a toe. The orthotic foot device may include a flexible insole chassis adapted to extend substantially between the heel and the toe of the footwear and one or more support components attached adjacent to one another at a lower side of the chassis. The chassis may include a cushioned layer composed of conforming resilient material overlying the upper side of the chassis. The footwear may also include sandals, boots or others.

In accordance with another embodiment of the present invention, there is provided an orthotic foot device for footwear including a flexible insole chassis adapted to extend substantially between the heel and the toe of the footwear and a hard plastic heel portion having an extending portion that partially wraps upwardly along one side of the chassis for protecting the fifth metatarsal of the foot of the wearer. The chassis may include a cushioned layer composed of conforming resilient material.

In accordance with yet another embodiment of the present invention, there is provided an arch support component for an orthotic foot device including a dished piece composed of suitable flexible material. The dished piece may include a generally crescent shaped bottom portion and having a side portion integrally connected to and intersecting with the bottom portion at a curved ridge having a midpoint. The bottom portion may be configured to accommodate the foot arch. An attachment side of the member may include at least one attachment device adapted to removably connect to the insole. Alternatively, the arch support component may be fixedly or integrally attached to the insole.

In accordance with another embodiment of the present invention, there is provided a method of making an orthotic foot device for footwear having a heel and a toe. The method may include creating a flexible insole chassis adapted to extend substantially between the heel and the toe of the footwear, and attaching at least one support component to a bottom side of the cushioned layer.

Figure 11:
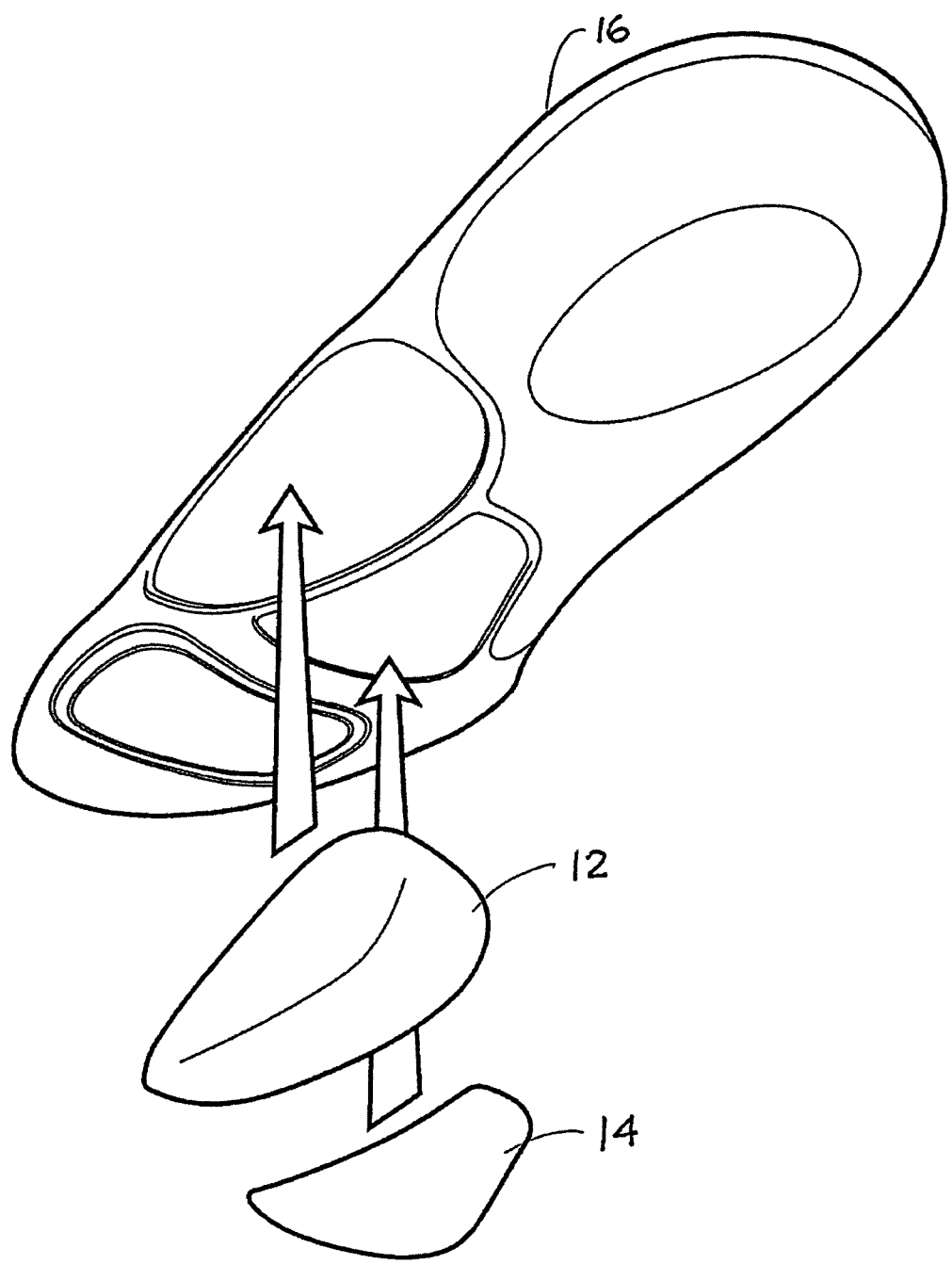
FIG. 11 is a pictorial view of the orthotic foot device of FIG. 1 showing the support components in the process of being attached in place.
Figure 12:
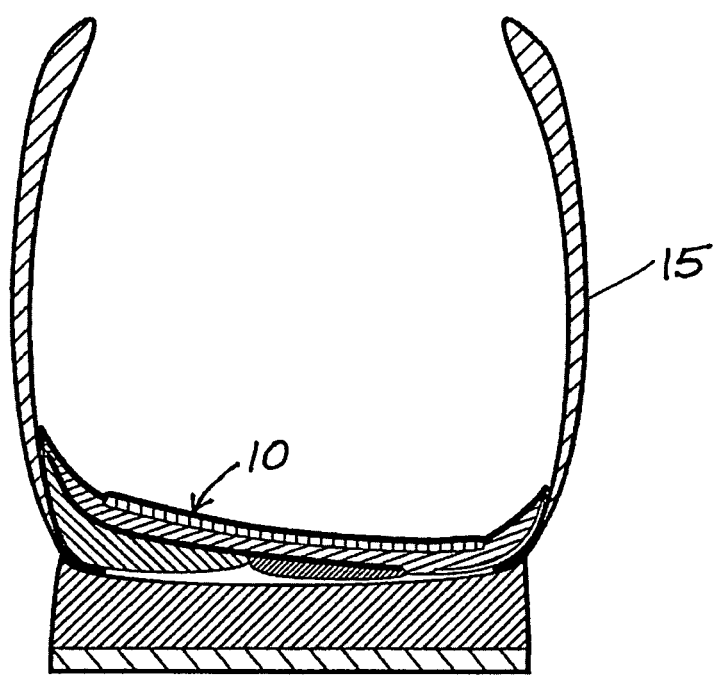
FIG. 12 is an enlarged sectional view of the orthotic foot device of FIG. 1 inserted within a shoe.
Figure 13:
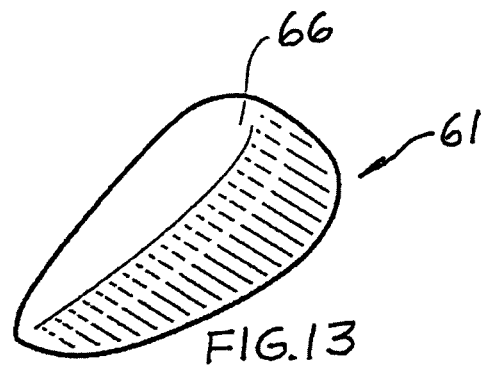
FIG. 13 is a pictorial view of the arch support for the orthotic foot device of FIG. 1.
Figure 14:
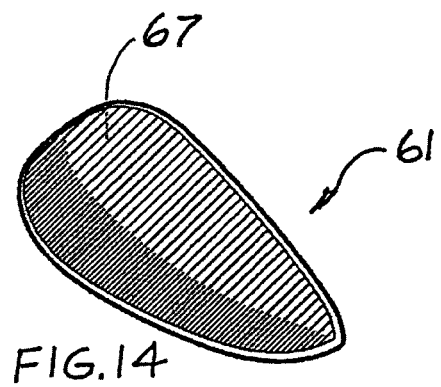
FIG. 14 is a bottom pictorial view of the arch support of FIG. 13.
Figure 21:
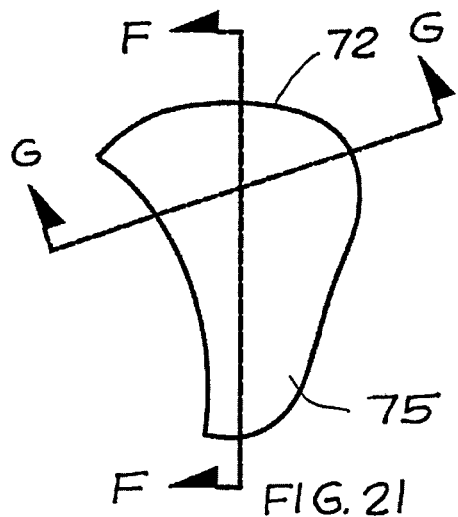
FIG. 21 is a top view of a metatarsal support, which provides light support for the orthotic foot device of FIG. 1.
Figure 25:
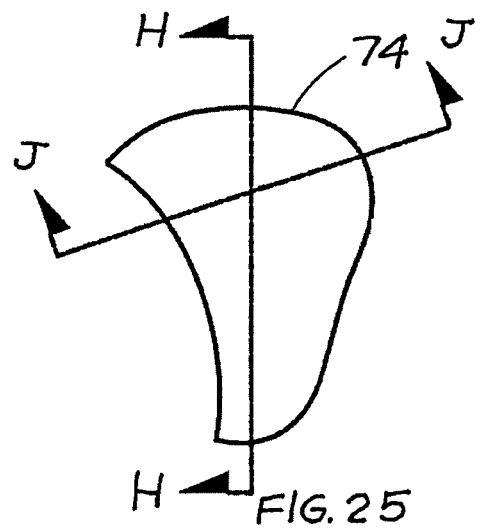
FIG. 25 is a top view of another metatarsal support, which provides medium support for the orthotic foot device of FIG. 1.
Figure 23:
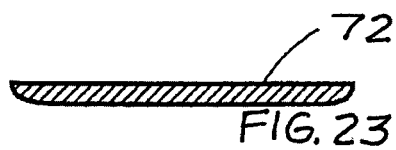
FIG. 23 is a sectional view of the metatarsal support of FIG. 21 taken along lines F-F thereof.
Figure 26:
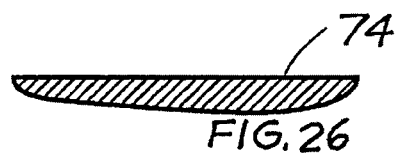
FIG. 26 is a sectional view of the metatarsal support of FIG. 25 taken on lines H-H thereof.
Figure 24:
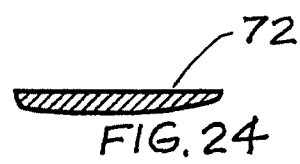
FIG. 24 is a sectional view of the metatarsal support of FIG. 21 taken along lines G-G thereof.
Figure 27:
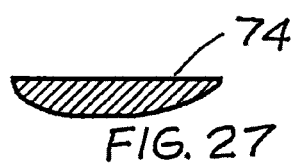
FIG. 27 is a sectional view of the metatarsal support of FIG. 25 taken on lines J-J thereof.
Figure 22:
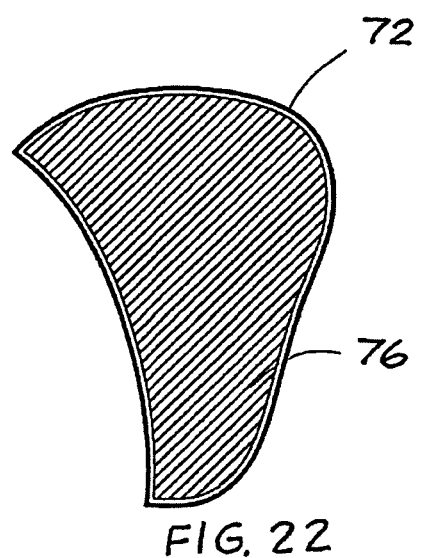
FIG. 22 is a bottom view of the metatarsal support of FIG. 21.

Referring to FIGS. 1 through 10, an orthotic foot device 10 preferably in the form of an insole is shown and may include a pair of removable support components, such as an arch support 12 and a metatarsal support 14, releasably attached to a footbed or insole chassis 16 that extends substantially the full length and breadth of a wearer's foot. Depending on the preference of the wearer, the arch support 12 and/or the metatarsal support 14 may be replaced with other similar arch supports and/or metatarsal supports which provide different amounts of support to accommodate the comfort and performance desired by the wearer as shown in FIG. 11. The orthotic foot device 10 may accommodate the desired comfort, protection, and support of the foot when inserted in footwear such as a shoe 15 as shown in FIG. 12.

The chassis 16 is elongated and may include a main structural layer 18 that extends substantially the full length and breadth of the foot, a heel layer 21 permanently attached to the bottom of the main structural layer 18, a cushioned layer 23 permanently attached to the top of the main structural layer 18, and a fabric layer 25 permanently attached to the top of the cushioned layer 23. The main structural layer 18 may include a cupped heel portion 27, a middle narrowed attachment portion 29, and an enlarged rounded toe portion 32. The main structural layer 18 may be at least partial composed of a flexible material, such as EVA or polyurethane.

The recessed or cupped heel portion 27 of the main structural layer 18 may be shaped or configured to receive the heel of the foot and partially wrapping around the side of the heel for support and protection of the heel.

The middle attachment portion 29 may be shaped to partially wrap around the side of the foot adjacent the arch of the foot and is recessed. The portion 29 includes an arch attachment region 34 adapted for removably receiving and attaching to the arch support 12, and a metatarsal attachment region 36 adapted for removably receiving and attaching the metatarsal support 14. The attachment regions 34 and 36 may include a plurality of loops 38 and 39, such as Velcro, or other removable connecting feature to interlock with a corresponding feature such as hooks on the supports 12 and 14, respectively.

The toe portion 32 may include a flexible, resilient area 41 to provide cushioning support to the toes and pad of the foot. The resilient area 41 may include a textured or roughened design to reduce slippage of the orthotic foot device 10 when placed in a shoe.

The heel layer 21 may include a hard plastic heel member 43 that may be shaped to correspond to the shape of the cupped heel portion 27 of the main structural layer 18 and a hard plastic extending leg 45 that extends along one side of the main structural layer 18 into the middle attachment portion 29. One side of the extend leg may be shaped in a complementary manner to edges of the support components 12, 14. The heel member 43 may protect the heel and lower portions of the side of the heel, while the extending leg 45 may protect the fifth metatarsal. The heel member 43 may also include an opening 47 in which a cushioned pad 49 may be inserted and permanently attached to the bottom of heel portion 27 of the main structural layer 18 to cushion the impact on the heel of the foot of the wearer. The cushioned pad 49 may be composed of a flexible resilient material such as a urethane gel or other suitable material to cushion.

The cushioned layer 23 may be permanently attached to the top or opposite side of the main structural layer 18 as is attached the heel layer 21. The cushioned layer 23 may be shaped substantially the same as the main structural layer 18, except that the cushioned layer 23 may not cover the areas of the main structural layer 18 that partially wrap upwardly around the side of the foot. The cushioned layer 23 may include a plurality of holes 52 to prevent the introduction of air bubbles into the orthotic foot device 10 during the fastening of the fabric layer 25 to the cushioned layer 23 by suitable means such as the application of a suitable adhesive material. The cushioned layer 23 may be composed of a conforming flexible resilient material having a slow rebound characteristic, such as a urethane foam material sold under the registered trademark Poron® by Rogers Corporation or Rogers, CT, or similar material, to provide added comfort and protection of the foot, and to reduce the sharpness in the edges of the support components 12, 14. The cushioned layer 23 may conform closely to the shape of the foot to fill in spaces or gaps, such as at the arch and around the toes, and to keep the entire foot in contact with the orthotic foot device 10. Poron is a performance urethane material which provides excellent shock absorption when walking, running, or performing other activities to help prevent foot fatigue. The material of the cushioned layer 23 compresses and conforms to the contours of the foot when weight is put on the foot, but immediately retains its original shape once the weight is removed. The thickness of the cushioned layer may be between the range of about 0.5 mm and about 10 mm. More preferably, the thickness may be about 3 mm. The wearer of the orthotic foot device 10 would select a chassis 16 that includes a cushioned layer 23 having their desired thickness as a matter of personal preference and comfort.

The fabric layer 25 of the chassis 16 may completely cover the cushioned layer 23 and the upwardly wrapping portions of the main structural layer 18. The fabric layer 25 may be composed of a thin natural or synthetic material, such as nylon or polyester, which absorbs moisture from the foot and helps to prevent the foot from sticking to the orthotic foot device 10. The fabric layer 25 may be treated with an antimicrobial agent to avoid foot odor/smelly shoes.

Figure 3:
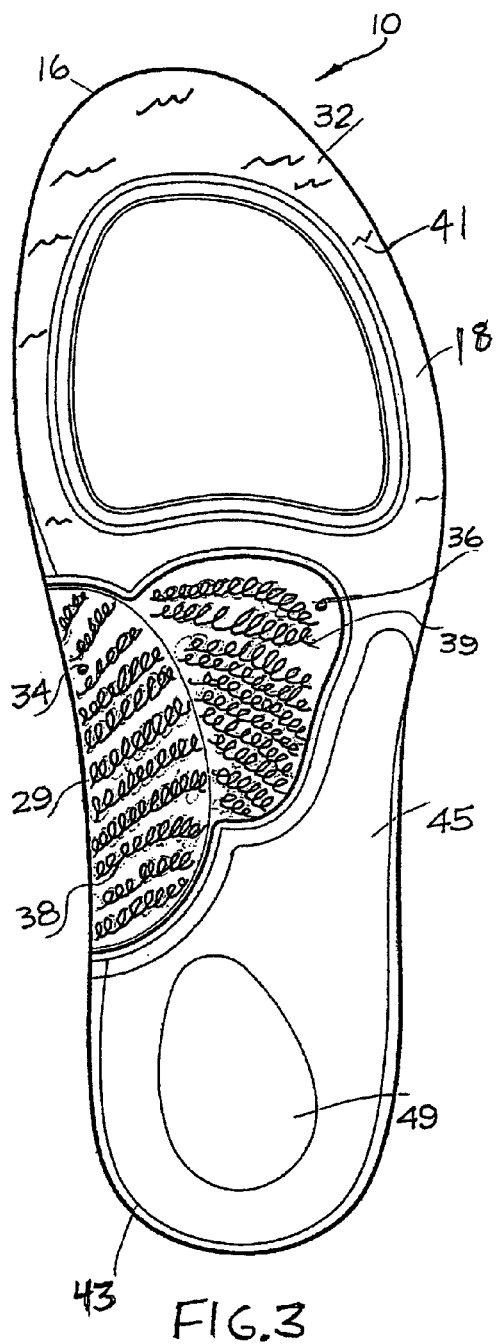
FIG. 3 is an enlarged view of the orthotic foot device of FIG. 1 with the support components removed.
Figure 4:
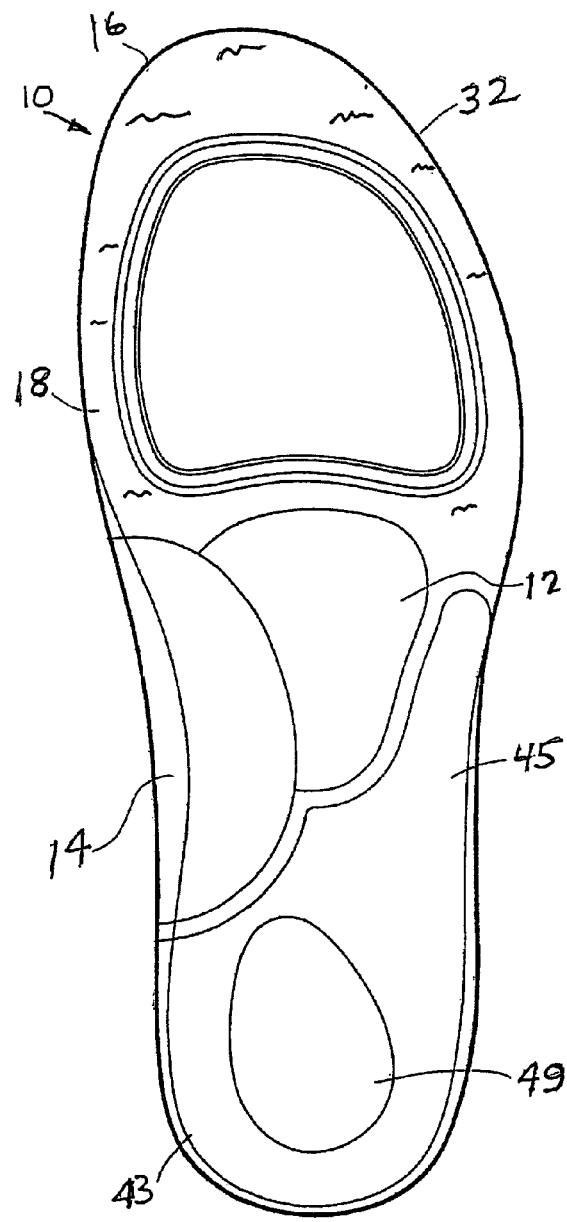
FIG. 4 is an enlarged view of the orthotic foot device of FIG. 1 with the support components attached.
Figure 7:
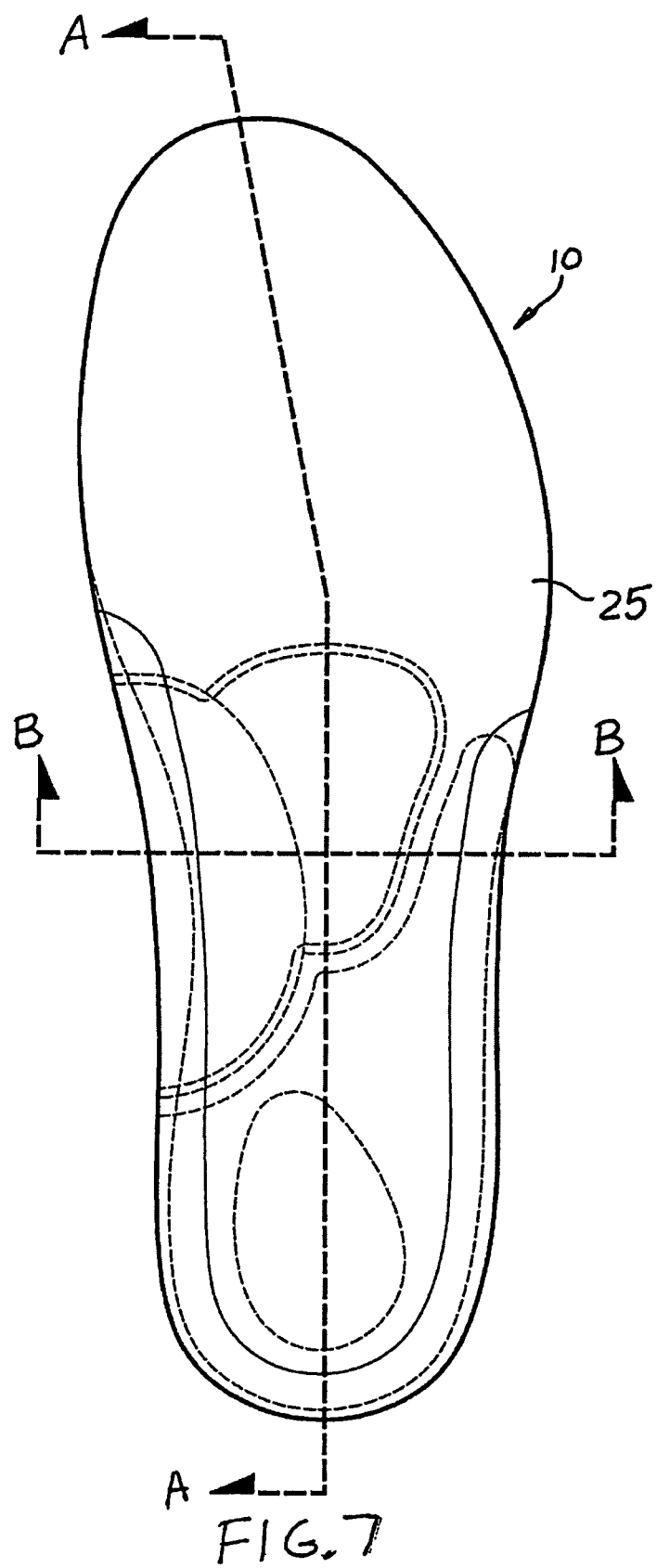
FIG. 7 is an enlarged top view of the orthotic foot device of FIG. 1.
Figure 8:
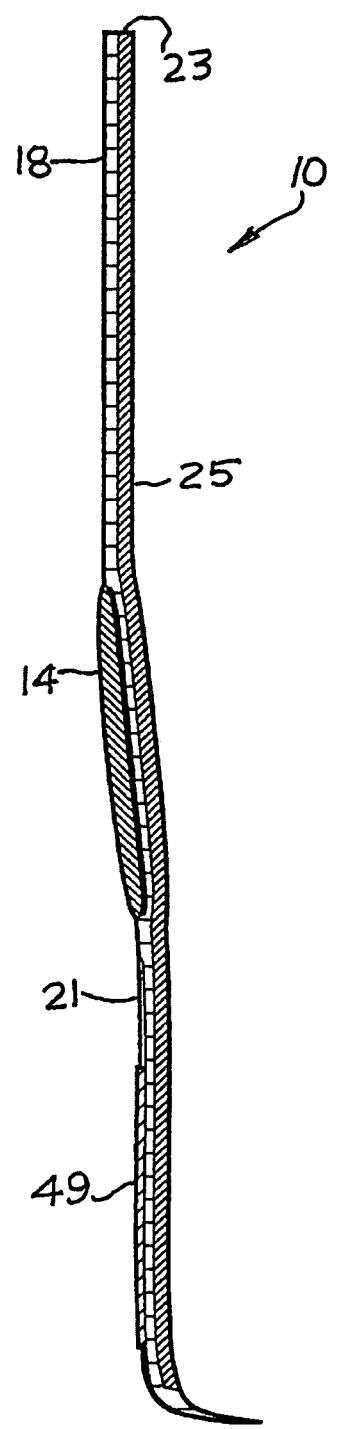
FIG. 8 is a sectional view of the orthotic foot device of FIG. 7 taken along lines A-A thereof.
Figure 9:
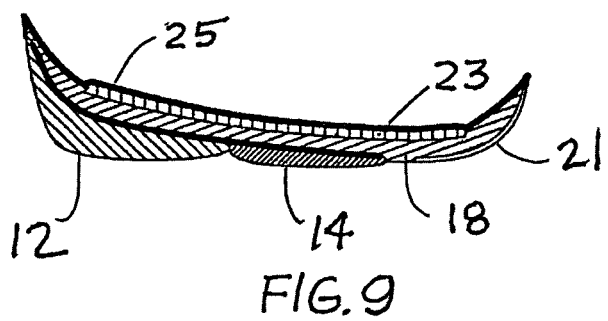
FIG. 9 is a sectional view of the orthotic foot device of FIG. 7 taken along lines B-B thereof.
Figure 10:
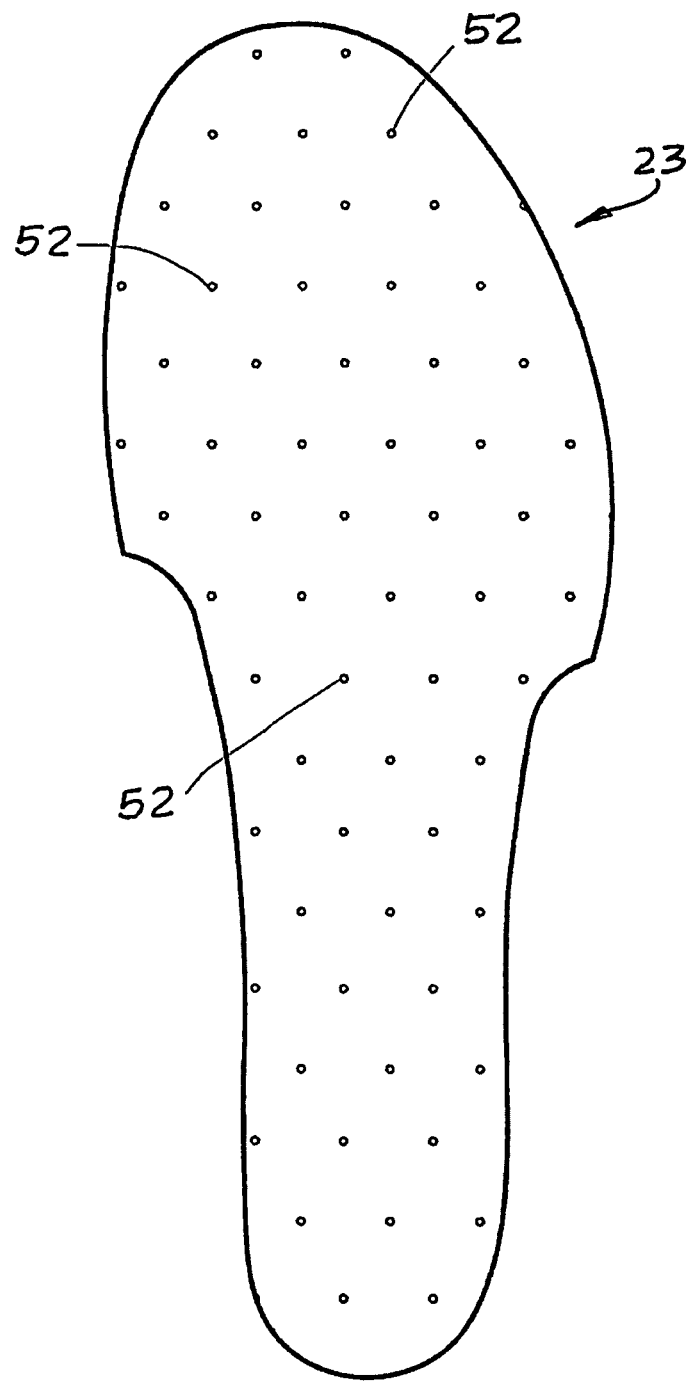
FIG. 10 is an enlarged top view of the cushion layer portion of the orthotic foot device of FIG. 2.

Referring now to FIGS. 13 through 20, a plurality of arch supports are shown that provide different amounts of arch support; a light arch support 61, a medium arch support 63, and a firm arch support 65. Each arch support may include a dished piece 66 made of a flexible material, such as EVA, urethane, or gel, and a fastener such as a plurality of hooks 67, such as Velcro, or other removable connecting feature on one side of the arch support for interlocking with the loops 38 of the attachment region 34 (FIG. 3). The thickness of the arch support may determine the amount of support and flexibility provided by the arch support. The light arch support 61 may include the thinnest dished shape or configuration having a C-shaped ridge 62 providing the lowest level of arch support and the most flexibility. The medium arch support 63 may include an intermediate thickness, which is dished shaped, having a C-shaped ridge 64 providing an intermediate level of arch support and less flexibility than the light arch support 61. The firm arch support 65 may include the thickest dished shape, having a C-shaped ridge 68 providing the greatest level of arch support and the least flexibility.

Referring now to FIGS. 21-27, a pair of metatarsal supports is shown that provide two different amounts of metatarsal support for the wearer. A light metatarsal support 72 and a medium metatarsal support 74 may be provided, but it should be understood that a different number may also be provided. Each metatarsal support may include a tear drop shaped piece 75 made of a flexible material, such as EVA, urethane, or gel, and a plurality of hooks 76 (FIG. 22), such as Velcro, or other removable connecting feature on one side of the metatarsal support for interlocking with the loops 39 of the attachment region 36 (FIG. 3). One portion of the tear drop shaped support may include a complementary shape to a portion of the arch support to allow metatarsal support and the arch support to be attached directly adjacent to one another. The thickness of the metatarsal support may determine the amount of support and flexibility provided by the metatarsal support. The light metatarsal support 72 may include the thinnest irregularly shaped piece providing the lowest level of metatarsal support and the most flexibility. The metatarsal support 74 may include a thicker dished piece providing a greater level of metatarsal support and less flexibility than the light metatarsal support 72.

A method of making the removable orthotic foot device may include the following steps. First, the insole chassis may be made, by creating a main structural layer, as described previously, that extends from the heel to the toe of a shoe using a suitable material. Next, the hard plastic heel portion having an opening may be fixedly attached to the cupped portion on the bottom of the main structural layer by a suitable fastener such as by applying a suitable adhesive. The cushioned pad may then be permanently attached within the opening of the heel portion to the main structural layer, also by a suitable fastener such as an adhesive.

Next, the material having loops, such as Velcro, or other removable connecting features may be attached to the attachment regions for the support components on the bottom of the main structural layer. The cushioned layer made of the conforming slow rebound resilient flexible material and substantially the same size as the main structural layer may then be attached or formed on the top of the main structural layer. The fabric layer may then be attached to the top of the cushioned layer and the upwardly extending portions of the main structural layer by a fastener such as a suitable adhesive. Lastly, the plurality of support components having different levels of support may be made using a suitable flexible material and including a portion of material having hooks, such as Velcro, or other complementary removable fastening feature attached to the underside of each support component for interlocking with the material having loops attached to the insole chassis. The support components may be made by a suitable process such as injection molding or other process.

The size of the insole chassis and the support components may vary due to the size and type of the shoe they are to be utilized within.

Words such as "about," "approximately" or other such words as used herein shall be defined to mean a tolerance of plus or minus 20 percent.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. An orthotic foot device for footwear having a heel and a toe, comprising:
   a flexible insole chassis being adapted to extend from the heel and toward the toe of the shoe and having upper and lower surfaces;
   the chassis including a cushioned portion composed of resilient material overlying at least a portion of the chassis for receiving the foot of the wearer in a closely conforming manner;
   an arch support component removably attached to the chassis to provide support to the foot of the wearer;
   a metatarsal support component removably attached to the chassis directly adjacent to the arch support component;
   the chassis having a recessed portion including both an arch support component receiving region configured in the shape of the arch support component and a metatarsal receiving region configured in the shape of the metatarsal support component disposed directly adjacent to one another to form a single recessed region for both components;
   the arch support component and the metatarsal support component being received within the single recessed region;
   one portion of the arch support component and one portion of the metatarsal support component being complementary shaped to enable the support components to directly fit together within the single component receiving recessed region directly adjacent to one another; and
   wherein the foot of the wearer is comfortable due to the closely conforming cushioned support and is supported from beneath the cushioned layer by the support component.

2. The orthotic foot device according to claim 1, further including a hard plastic heel portion having an extending portion that partially wraps upwardly along a side of the chassis for protecting the fifth metatarsal.

3. The orthotic foot device according to claim 2, wherein the hard plastic heel portion includes an opening for a heel pad.

4. The orthotic foot device according to claim 3, wherein the heel pad is composed of a urethane gel.

5. The orthotic foot device according to claim 1, wherein the arch support partially wraps upwardly along another side of the chassis for supporting and protecting the arch.

6. The orthotic foot device according to claim 1, wherein the cushioned portion has a thickness of between about 0.5 mm and about 10 mm.

7. The orthotic foot device according to claim 1, further including a fabric layer attached to a top side of the cushioned layer.

8. An orthotic foot device for footwear according to claim 1, comprising:
   wherein the chassis including a cushioned portion composed of conforming resilient material; and
   a hard plastic heel portion having an extending portion that partially wraps upwardly along one side of the chassis for protecting the fifth metatarsal.

9. The orthotic foot device according to claim 8, wherein the hard plastic heel portion includes an opening for a heel pad.

10. The orthotic foot device according to claim 9, wherein the heel pad is composed of a urethane gel.

11. The orthotic foot device according to claim 1, wherein at least one of the support components is:
   a dished piece composed of suitable flexible material;
   the dished piece having an attachment side and being dished on the attachment side thereof for engaging the chassis and having a generally crescent shaped bottom portion and having a side portion integrally connected to and intersecting with the bottom portion at a curved ridge having a midpoint;
   the dished piece having a cross sectional thickness and the cross sectional thickness of the dished piece at the midpoint of the curved ridge defining the amount of support and flexibility of the arch support component;
   the bottom portion being configured to accommodate the foot arch; and
   the attachment side of the piece including at least one attachment device adapted to removably connect to the chassis.

12. The arch support component according to claim 11, wherein the attachment device includes hooks.

13. A method of making a removable orthotic foot device for a shoe having a heel and a toe, comprising:
   providing a flexible insole chassis adapted to extend from the heel toward the toe of the shoe and having a recessed portion including both an arch support component receiving recessed region configured in the shape of the arch support component and a metatarsal support receiving recessed region configured in the shape of the metatarsal support component disposed directly adjacent to one another to form a single recessed region for both components;
   removably attaching an arch support component to the insole chassis at within the arch support recessed receiving region of the recessed portion;
   removably attaching a metatarsal support component to the chassis directly adjacent to the arch support component at within the metatarsal support recessed receiving region of the same recessed portion; and
   fitting together complementary portions of the arch support components and the metatarsal support components within the recessed portion.

14. The method according to claim 13, further including attaching a cushioned layer to a top side of the insole chassis.

15. The method according to claim 14, wherein the cushioned layer includes a fabric layer attached to a top side of the cushioned layer.

* * * * *

UNITED STATES PATENT AND TRADEMARK OFFICE
CERTIFICATE OF CORRECTION

PATENT NO. : 8,453,346 B2  Page 1 of 1
APPLICATION NO. : 12/196113
DATED : June 4, 2013
INVENTOR(S) : Michael Steszyn et al.

It is certified that error appears in the above-identified patent and that said Letters Patent is hereby corrected as shown below:

In the Claims:

Claim 13, column 8, line 15, delete "at".

Claim 13, column 8, line 19, delete "at".

Signed and Sealed this
Seventeenth Day of September, 2013

Teresa Stanek Rea
*Deputy Director of the United States Patent and Trademark Office*